(12) United States Patent
Devassy et al.

(10) Patent No.: US 9,162,215 B2
(45) Date of Patent: Oct. 20, 2015

(54) METHODS FOR PRODUCING EPOXIDATION CATALYSTS AND EPOXIDATION METHODS UTILIZING THESE

(71) Applicants: Biju M. Devassy, Karukutty (IN); Albert C. Liu, Charleston, WV (US); Hwaili Soo, Charleston, WV (US)

(72) Inventors: Biju M. Devassy, Karukutty (IN); Albert C. Liu, Charleston, WV (US); Hwaili Soo, Charleston, WV (US)

(73) Assignee: DOW TECHNOLOGY INVESTMENTS LLC, Midland, MI (US)

( * ) Notice: Subject to any disclaimer, the term of this patent is extended or adjusted under 35 U.S.C. 154(b) by 0 days.

(21) Appl. No.: 14/354,126

(22) PCT Filed: Oct. 4, 2012

(86) PCT No.: PCT/US2012/058755
§ 371 (c)(1),
(2) Date: Apr. 24, 2014

(87) PCT Pub. No.: WO2013/066557
PCT Pub. Date: May 10, 2013

(65) Prior Publication Data
US 2014/0371470 A1    Dec. 18, 2014

Related U.S. Application Data

(60) Provisional application No. 61/553,577, filed on Oct. 31, 2011.

(51) Int. Cl.
| | | |
|---|---|---|
| *C07C 29/10* | (2006.01) | |
| *C07C 41/03* | (2006.01) | |
| *B01J 23/50* | (2006.01) | |
| *B01J 23/66* | (2006.01) | |
| *B01J 35/10* | (2006.01) | |
| *B01J 37/02* | (2006.01) | |
| *B01J 23/68* | (2006.01) | |
| *C07D 301/10* | (2006.01) | |
| *C07C 213/04* | (2006.01) | |
| *C07D 317/04* | (2006.01) | |

(52) U.S. Cl.
CPC ............. *B01J 23/688* (2013.01); *B01J 23/50* (2013.01); *B01J 23/66* (2013.01); *B01J 35/1009* (2013.01); *B01J 35/109* (2013.01); *B01J 35/1076* (2013.01); *B01J 37/0201* (2013.01); *B01J 37/0205* (2013.01); *C07C 29/106* (2013.01); *C07C 41/03* (2013.01); *C07C 213/04* (2013.01); *C07D 301/10* (2013.01); *C07D 317/04* (2013.01); *B01J 23/683* (2013.01); *B01J 35/108* (2013.01)

(58) Field of Classification Search
CPC ........ C07C 29/106; C07C 41/03; B01J 23/50; B01J 23/66; B01J 35/1009; B01J 35/1076; B01J 35/109; B01J 37/0205
See application file for complete search history.

(56) References Cited

U.S. PATENT DOCUMENTS

| | | | |
|---|---|---|---|
| 3,575,888 A | 4/1971 | Long | |
| 3,702,259 A | 11/1972 | Nielsen | |
| 4,102,820 A | 7/1978 | Cavitt | |
| 4,242,235 A | 12/1980 | Cognion | |
| 4,248,741 A * | 2/1981 | Wernli et al. | 502/341 |
| 4,305,844 A | 12/1981 | Vangermain | |
| 4,812,437 A | 3/1989 | Nojiri | |
| 4,916,243 A | 4/1990 | Bhasin | |
| 5,063,195 A | 11/1991 | Jin | |
| 5,173,469 A * | 12/1992 | Wunde et al. | 502/340 |
| 5,187,140 A | 2/1993 | Thorsteinson | |
| 6,831,037 B2 | 12/2004 | Szymanski | |
| 7,560,577 B2 | 7/2009 | Hirota | |
| 7,714,152 B2 | 5/2010 | Pak | |
| 2009/0131695 A1 | 5/2009 | Gerdes | |
| 2009/0177000 A1 | 7/2009 | Natal | |
| 2009/0177016 A1 | 7/2009 | Lockemeyer | |
| 2009/0198076 A1 | 8/2009 | Guckel | |
| 2010/0016617 A1 * | 1/2010 | Pak et al. | 502/340 |

FOREIGN PATENT DOCUMENTS

| | | | |
|---|---|---|---|
| CN | 1634652 | 7/2005 | |
| EP | 0266015 | 12/1991 | |
| WO | 2006133183 | 12/2006 | |
| WO | WO 2006/133183 | * 12/2006 | ........... C07D 301/10 |
| WO | 2007085206 | 8/2007 | |
| WO | 2012140614 | 10/2012 | |

* cited by examiner

*Primary Examiner* — Erich A Leeser
(74) *Attorney, Agent, or Firm* — Edward L. Brant; KSJLAW, LLC

(57) ABSTRACT

Methods are provided for producing epoxidation catalysts. The present methods are able to produce catalysts having the desired loading levels of catalytic species at a lower vacuum level (having a higher minimum residual pressure) than previously appreciated by the art, thereby providing equipment cost and time savings.

9 Claims, 3 Drawing Sheets

METHODS FOR PRODUCING EPOXIDATION CATALYSTS AND EPOXIDATION METHODS UTILIZING THESE

FIELD OF THE INVENTION

Provided herein are methods for producing epoxidation catalysts. Advantageously and unexpectedly, the method is capable of depositing optimized amounts of a catalytic species onto a support using a cost effective vacuum level.

BACKGROUND

Catalysts are important components of many chemical manufacturing processes, and may typically be used to accelerate the rate of the reaction in question and/or to increase the selectivity or efficiency towards the desired product(s). Utilized in connection with many reactions, catalysts find particularly advantageous use in the epoxidation of olefins, a process of significant commercial importance in the commodity chemical business. In epoxidation reactions, a feed containing at least the olefin and oxygen is contacted with a catalyst causing the formation of the corresponding olefin oxide.

One example of an olefin epoxidation of particular commercial importance is the epoxidation of alkylenes, or mixtures of alkylenes, and this epoxidation reaction in particular can rely upon high performing catalysts in order to be commercially viable. Those of skill in the art have actively sought improvements in the efficiency and/or activity of epoxidation catalysts for some time, since, on a commercial scale, even slight, e.g., 1%, increases in selectivity can substantially reduce the operating costs associated with the epoxidation processes.

One method thought to be capable of improving catalyst performance is the impregnation thereupon of an optimized amount of a catalytic species. The amount of such catalytic species capable of being deposited onto a carrier, in turn, is thought to be related to one or more of surface area, pore size distribution, water absorption, and total pore volume of the catalyst support. And so, many efforts have focused on providing a support having a combination of these properties that not only provides a sufficiently robust support to be commercially useful, but that also may readily be impregnated with the desired amount of catalytic species.

Very little attention has been paid to the particular conditions of the impregnation, and the impact of the same on the amount of catalytic species ultimately deposited, although it is generally thought that conducting the impregnations under conditions of a fairly high vacuum is required. More particularly, high vacuum levels, i.e., vacuum levels having low minimum residual pressures, e.g., of no more than 1-2 inches mercury, absolute (34-68 mbar), are recognized in the art as being required in order to remove trapped air from the pores of the support and to thus assist in the permeation of the catalytic species, or a precursor thereof, therein.

However, the use of excessive vacuum levels can add undesirable equipment cost, as well as time, to a catalyst production process. It would be beneficial to provide a method of providing such catalysts that can utilize supports having the desired characteristics, achieve the desired level of catalytic species loading, while yet, utilizing fewer resources.

SUMMARY OF THE INVENTION

The present invention provides such methods. More particularly, it has now been surprisingly discovered that desired levels of catalyst species loading, e.g., from 80% to 98% of a maximum loading, can be obtained even if the supports upon which the catalytic species, or a precursor thereof, is to be impregnated upon are evacuated to a lesser level of vacuum having a higher minimum residual pressure than appreciated by the art as being required to achieve the same. This is unexpected since it has previously been thought that as surface areas trend upward and pore sizes commensurately trend downward in the art, higher vacuums having lower minimum residual pressures would need to be drawn in order to evacuate air therefrom, and to assist in the permeation of the impregnation solution there into in order to provide the desired loading levels. The present methods are able to produce catalysts having the desired loading levels of catalytic species at a lesser vacuum level (having a higher minimum residual pressure) than previously appreciated by the art, thereby providing equipment cost and time savings.

In a first aspect, the present invention provides a method of providing an epoxidation catalyst. The method comprises exposing a porous carrier to a vacuum having a minimum residual pressure of greater than 135 mbar, absolute, and contacting the carrier with an impregnation solution comprising a catalytic species, or a precursor thereof, while so exposed. And, in some embodiments, the contact may also occur at temperatures of less than 50° C., or less than 40° C., or less than 35° C. Further, the exposing, the contacting, or both, may be carried out more than once, if desired, and in some embodiments, may be carried out two or more times. The minimum residual pressure of the vacuum may typically be less than 1000 mbar, absolute. The carrier so prepared may be further processed by exposing the same to an elevated temperature of, e.g., at least 200° C. following separation from the excess, i.e. non-impregnated, impregnation solution.

The method is expected to be beneficial to any carrier useful as a catalyst support, regardless of the physical properties thereof. However, in some embodiments, particular benefit may be provided to carriers i) having a surface area of at least 1.1 $m^2/g$ and/or ii) having at least 5% of its total pore volume being present in pores having a pore diameter of greater than 3 microns and/or iii) having at least two pore size distribution peaks in the pore diameter range of from 0.01 microns to 100 microns and having a median pore diameter of greater than 1.1 micron.

Furthermore, the method is expected to be useful to provide any desired catalyst, comprising any desired catalytic species. In some embodiments, an epoxidation catalyst is provided, and in such embodiments, the catalytic species may desirably comprise silver. In such cases, and depending on the properties of the carrier, a catalytic species loading of at least 10 wt. % Ag, or at least 14 wt. % Ag, or even at least 18 wt. % Ag, the weight percentages being based on the total weight of the epoxidation catalyst, can be provided on the carrier after a single sequence of exposing, contacting, and processing at elevated temperature. Epoxidation catalysts typically comprise one or more promoters, and so, the impregnation solution may include the same. In some embodiments, the one or more promoters may include rhenium, molybdenum, tungsten, lithium, sulfur, manganese, rubidium, cesium, sodium, potassium, or combinations of these. In other embodiments, the one or more additional promoters may comprise rhenium and/or cesium.

Epoxidation catalysts produced by the present method are expected to exhibit advantageous properties due to the inclusion thereupon of a desirable catalytic species loading, and are further expected to be capable of production at a cost savings relative to conventional methods that employ much higher vacuum levels having much lower minimum residual pressures. And so, in another aspect, an epoxidation catalyst prepared according to the method is provided.

The advantageous catalytic species loading, and cost savings provided by the present method are not only expected to translate to improvements in one or more catalyst properties, but also, are expected to provide improvements to the processes in which the catalysts are utilized. As a result, and in yet another aspect, the present invention provides a process for the epoxidation of an alkylene. The process comprises reacting a feed comprising one or more alkylenes and oxygen in the presence of a catalyst prepared according to the method.

The advantages provided to such processes can be further leveraged by utilization of the alkylene oxides produced thereby in further downstream processes, and such processes are thus provided in yet another aspect of the invention. More specifically, the present invention also provides a process for preparing a 1,2-diol, a 1,2-diol ether, a 1,2-carbonate, or an alkanolamine. The process comprises converting an alkylene oxide into the 1,2-diol, 1,2-diol ether, a 1,2-carbonate, or alkanolamine, wherein the alkylene oxide is prepared by a process utilizing a catalyst prepared according to the method.

DESCRIPTION OF THE DRAWINGS

These and other features, aspects and advantages of the present invention may be further understood and/or illustrated when the following detailed description is considered along with the attached drawings.

DETAILED DESCRIPTION OF THE INVENTION

Figure 1A:
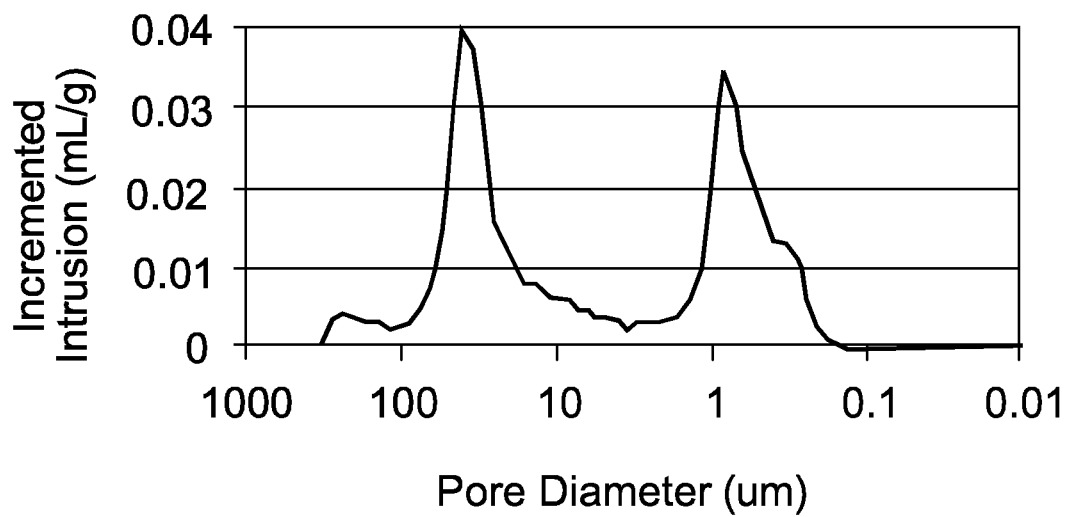
FIG. 1A is a graphical depiction of the pore size distribution of a carrier A to be subjected to a method according to one embodiment.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof; rather, and unless otherwise noted, terms are to be understood according to conventional usage by those of ordinary skill in the relevant art.

Unless defined otherwise, technical and scientific terms used herein have the same meaning as is commonly understood by one of skill in the art to which this invention belongs. The "selectivity" of an epoxidation reaction, which is synonymous with "efficiency," refers to the fraction, expressed as a percentage, of converted or reacted olefin that forms the corresponding olefin oxide product. The terms "efficiency" and "selectivity" are used interchangeably herein. The activity of an epoxidation reaction can be quantified in a number of ways, one being the mole percent of olefin oxide contained in an outlet stream of the reactor relative to that in an inlet stream (the mole percent of olefin oxide in the inlet stream typically, but not necessarily, approaches zero percent) while the reactor temperature is maintained substantially constant; and another being the temperature required to maintain a given rate of olefin oxide production. In many instances, activity is measured over a period of time in terms of the mole percent of olefin oxide produced at a specified constant temperature. Alternatively, activity can be measured as a function of the temperature required to sustain production of a specified constant mole percent of olefin oxide.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.).

Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments. As used herein, the phrase "minimum residual pressure", means the lowest pressure produced within an impregnation vessel and/or the porous carriers that may be contained therein for purposes of impregnating the same.

The present invention provides methods of providing an epoxidation catalyst. More specifically, the method involves exposing a porous carrier to a vacuum having a minimum residual pressure of greater than 135 mbar, absolute, and contacting the carrier to an impregnation solution comprising a catalytic species, or a precursor thereof.

It has now been surprisingly discovered that use of such a vacuum, as opposed to the much higher vacuums having much lower minimum residual pressures taught by the prior art, can yet provide the carriers with a commercially acceptable or desired catalytic species loading. Because evacuation to the low minimum residual pressures described in the prior art is not required, less costly equipment can be used to provide a suitable vacuum level, and less energy may be required to operate it. And so, the catalysts produced by the present method may perform at least as well, or even better, in epoxidation processes than those produced via conventional methods, while also being cheaper to produce.

More particularly, the vacuums now unexpectedly found to be useful, and employed in the present methods, may typically correspond to a minimum residual pressure of greater than 135 mbar, absolute, or greater than 200 mbar absolute, or greater than 300 mbar absolute, or greater than 400 mbar absolute, or greater than 600 mbar absolute, or greater than 800 mbar absolute. Stated another way, in some embodiments, the vacuum may correspond to a minimum residual pressure of less than 1000 mbar, absolute, or less than 800 mbar absolute, or less than 600 mbar, absolute, or less than 400 mbar absolute, or less than 200 mbar absolute, or even less than 150 mbar absolute.

At least a portion of the contacting is desirably carried out while the carrier is exposed to the vacuum. That is, the carrier may be removed from the impregnation solution before the vacuum is removed, while the vacuum is removed, or after the vacuum is removed. Stated another way, the vacuum may be applied to an impregnation vessel already containing an impregnation solution, and the carrier thereafter added to the vessel while maintaining the vacuum, or, the carrier may be added to an impregnation vessel containing an impregnation solution, and the vacuum applied thereafter. In more preferred embodiments, the carrier may be placed in an impregnation vessel to which the impregnation solution is thereafter added, following which the vacuum is then applied, or, most preferably, the carrier may be placed in an impregnation vessel to which the vacuum is thereafter applied, following which the impregnation solution is then introduced while maintaining the vacuum. Regardless of the particular sequence of steps, so long as at least some portion of the contact occurs while the carrier is exposed to the vacuum, the vacuum having a minimum residual pressure of greater than 135 mbar, absolute, during at least this overlapping period of both contacting and exposing, at least some portion of the benefits of the present methods are expected to be provided.

Further, the contacting may be carried out at impregnation solution temperatures of less than 50° C., or less than 40° C., or even less than 35° C., if desired. Such temperature limitations may be useful in embodiments wherein the desired impregnation solution comprises thermally sensitive components. For example, in those embodiments wherein the catalytic species desirably comprises silver, it may be advantageous to limit the solution temperature during contacting to less than 50° C. since soluble silver may be reduced to silver metal at temperatures greater than 50° C.

Multiple impregnations may be carried out, and in those embodiments wherein the same is desired, any additional impregnations may or may not be carried out under vacuum, or under the same vacuum level as an earlier impregnation performed on the carrier exposed to the vacuum. All that is required for the benefits of the present method to be realized is that at least one impregnation is carried out on a carrier while exposed to a vacuum having a minimum residual pressure of greater than 135 mbar, absolute. In other embodiments, two impregnations may be performed, the carriers removed from the vacuum and exposed to the same, or a different, level of vacuum for the second impregnation.

Typically, when the catalytic species comprises silver, a reduction step is conducted during or after the impregnations, to form metallic silver particles. Such a reduction step may typically comprise exposing the impregnated carrier to an elevated temperature of, e.g., at least 200° C., or at least 250° C., or at least 300° C., or at least 350° C., or even at least 400° C., or 500° C., or higher. Exposure to such an elevated temperature can have the effect of depositing the catalytic species on the support. The carrier will desirably be exposed to the elevated temperature for a time period sufficient to so provide, e.g., for a time period of at least 2 minutes, or at least 2.5 minutes, or at least 5 minutes, or at least 10 minutes, or even longer.

The method is expected to be beneficial to any carrier useful as a catalyst support, regardless of the physical properties thereof. However, in some embodiments, particular benefit may be provided to carriers i) having a surface area of at least 1.1 $m^2/g$ and/or ii) having at least 5% of its total pore volume being present in pores having a pore diameter of greater than 3 microns and/or iii) having at least two pore size distribution peaks in the pore diameter range of from 0.01 microns to 100 microns and having a median pore diameter greater than 1.1 micron. See, e.g., FIG. 1A for a graphical depiction of a carrier having at least two pore size distribution peaks within this range. In certain preferred embodiments, benefits may be provided to carriers having a surface area of at least 1.1 $m^2/g$ and having at least 5%, or at least 10%, or at least 15%, or even at least 20% of its total pore volume being present in pores having a pore diameter of greater than 3 microns.

"Surface area," as used herein, refers to the surface area of the carriers as determined by the BET (Brunauer, Emmett and Teller) method by nitrogen as described in the Journal of the American Chemical Society 60 (1938) pp. 309-316. "Total pore volume" means pore volume of the carrier and is typically determined by mercury porosimetry. The measurements reported herein used the method described in Webb & Orr, Analytical Methods in Fine Particle Technology (1997), p. 155, using mercury intrusion to 60,000 psia using Micrometrics Autopore IV 9520, assuming 130° contact angle, 0.485 N/M surface tension of Hg. "Porosity" is the proportion of the non-solid volume to the total volume of material. Total pore volume as measured by mercury porosimetry or water absorption may be used to estimate porosity by those of skill in the art. Put another way, porosity is defined as the void volume (unoccupied space) divided by the total volume of the sample. "Median pore diameter" means the pore diameter corresponding to the point in the pore size distribution at which half of the total pore volume of the carrier has cumulatively been measured.

The carriers may comprise any of the large number of porous refractory structure or support materials, so long as whatever the porous refractory material chosen, it is relatively inert in the presence of the chemicals and processing conditions employed in the application in which the carriers will be utilized.

The carriers may be prepared from precursor compositions comprising, for example, any of the transition alumina precursors, transition aluminas, hydrated aluminum compounds, alpha-alumina, silicon carbide, silicon dioxide, zirconia, zirconium silicate, graphite, magnesia and various clays.

As used herein, "transition alumina precursors" are one or more materials that, upon thermal treatment, are capable of being at least partially converted to transition alumina. Transition alumina precursors include, but are not limited to, aluminum tri-hydroxides, such as gibbsite, bayerite, and nordstrandite; and aluminum oxide hydroxides, such as boehmite, pseudo-boehmite and diaspore. "Transition aluminas" are one or more aluminas other than alpha-alumina, which are capable of being at least partially converted to alpha-alumina under thermal treatment at 900° C. or greater. Transition aluminas possess varying degrees of crystallinity, and include, but are not limited to gamma-alumina, delta-alumina, eta-alumina, kappa-alumina, chi-alumina, rho-alumina, and theta-alumina. "Alpha-alumina precursor" means one or more materials capable of being transformed into alpha-alumina, including transition alumina precursors and transition aluminas.

In those embodiments of the invention wherein precursors of the carriers comprise one or more transition alumina precursors, transition aluminas, or other alpha-alumina precursors, the carriers may desirably be fluoride affected, as may be achieved by incorporating therein or exposing the carriers to fluorine-containing species, as may be provided in gaseous form, in gaseous or liquid solution, or via the provision of solid fluorine-containing source operatively disposed relative to the carriers. For advantages provided in processing, any such fluoride effect may desirably be achieved via exposure of the carriers to one or more fluorine-containing species in gaseous form or in gaseous solution. The particulars of such gaseous fluoride affectation are described in copending, commonly assigned PCT application no. PCT/US2006/016437.

The carriers may also comprise other organic compounds e.g., binders and dispersants (such as those described in *Introduction to the Principles of Ceramic Processing*, J. Reed, Wiley Interscience, 1988), or pore formers, to facilitate the shaping, or to alter the porosity, of the carriers. Pore formers (also known as burn out agents) are materials used to form specially sized pores in the carriers by being burned out, sublimed, or volatilized. Pore formers are generally organic, such as ground walnut shells, granulated polyolefins, such as polyethylene and polypropylene, but examples of inorganic pore formers are known. The pore formers are usually added to the carrier raw materials prior to shaping. During a drying or calcining step or during the conversion of the alpha-alumina precursor to alpha-alumina, the pore formers may typically be burned out, sublimed, or volatilized. In some embodiments of the present catalysts, the pore size distribution and surface area of the carriers may advantageously be provided without the use of such pore formers, thereby eliminating the cost and processing time associated with their use.

Whatever the raw materials selected for use in preparing the carriers, they are desirably of sufficient purity so that there are limited undesired reactions between any of them. Any impurities are not present in a quantity sufficient to substantially detrimentally impact the properties of the carriers and/or catalysts based thereupon. In particular, any impurities are desirably limited to not more than 3 wt. %, or even not more than 1.5 wt. %, of the total weight of the carriers.

The carriers may be formed according to any suitable known method known to those of ordinary skill in the chemical engineering art. Typically, the desired components of the carriers, i.e., at least the desired refractory support materials, are first combined, in any form and any order, by any suitable method known in the art. Examples of suitable techniques for combining the carrier materials include ball milling, mix-mulling, ribbon blending, vertical screw mixing, V-blending, and attrition milling. The mixture may be prepared dry (i.e., in the absence of a liquid medium) or wet.

Once mixed, the carrier materials may be formed by any suitable method, such as e.g., injection molding, extrusion, isostatic pressing, slip casting, roll compaction and tape casting. Each of these is described in more detail in *Introduction to the Principles of Ceramic Processing*, J. Reed, Chapters 20 and 21, Wiley Interscience, 1988. Suitable shapes for the carriers generally can include without limitation pills, chunks, tablets, pieces, spheres, pellets, tubes, wagon wheels, toroids having star shaped inner and outer surfaces, cylinders, hollow cylinders, amphora, rings, Raschig rings, honeycombs, monoliths, saddles, cross-partitioned hollow cylinders (e.g., having at least one partition extending between walls), cylinders having gas channels from side wall to side wall, cylinders having two or more gas channels, and ribbed or finned structures. If cylinders, the carriers may be circular, oval, hexagonal, quadrilateral, or trilateral in cross-section. In those embodiments of the invention wherein the carriers are intended for end use as catalysts, the carriers may desirably be formed into a rounded shape, e.g., pellets, rings, tablets and the like, having diameters of from 0.1 inch (0.25 cm) to 0.8 inch (2 cm).

Carriers so formed may then optionally be heated under an atmosphere sufficient to remove water, decompose any organic additives, or otherwise modify the precursors prior to introduction into a kiln, oven, pressure-controlled reaction vessel or other container for any further treatment required for processing into carriers. Suitable atmospheres include, but are not limited to, air, nitrogen, argon, hydrogen, carbon dioxide, water vapor, those comprising fluorine-containing gases or combinations thereof.

In some embodiments, the carriers may desirably be washed to remove any soluble residues thereon prior to the deposition of the components of the end-use product based thereupon. There is some indication that washed carriers may exhibit at least marginally enhanced performance, although unwashed carriers are also often successfully used in end-use products. If washing is desired, the carriers may be washed with hot, e.g., from 80° C. to 100° C., demineralized water until the electrical conductivity of the effluent water does not decrease.

Once so formed, the carriers are transformed into the desired catalysts via an impregnation and deposition thereupon of the desired catalytic species, or a precursor thereof. According to the present method, this impregnation occurs under a vacuum corresponding to a minimum residual pressure of greater than 135 mbar, absolute. The vacuum may be applied to an impregnation vessel already containing an impregnation solution, and the carrier thereafter added to the vessel while maintaining the vacuum, or, the carrier may be added to an impregnation vessel containing an impregnation solution, and the vacuum applied thereafter.

In more preferred embodiments, the carrier may be placed in an impregnation vessel to which the impregnation solution is thereafter added, following which the vacuum is then applied, or, most preferably, the carrier may be placed in an impregnation vessel to which the vacuum is thereafter applied, following which the impregnation solution is then introduced while maintaining the vacuum. Regardless of the particular sequence of steps, in some preferred embodiments, the impregnated carrier is thereafter separated from the excess impregnation solution and then processed, for example, by treatment at elevated temperatures, in order to deposit the desired catalyst species.

Once deposited, the catalytic species can be bound directly on the surface of the carriers, or, the catalytic species may be bound to a washcoat, i.e., another surface which has been applied to the surface of the carriers. The catalytic species may also be covalently attached to a macromolecular species, such as synthetic polymer or a biopolymer such as a protein or nucleic acid polymers, which in turn, is bound either directly to the surface of the carriers or a washcoat applied thereto. Further, a deposited catalytic species may reside on the surface of the carriers, be incorporated into a lattice provided on the surface of the carriers, or be in the form of discrete particles otherwise interspersed among the carriers.

Non-limiting examples of catalytic species that may advantageously be supported by the carriers include metals, solid state compounds, molecular catalysts, enzymes and combinations of these. Metals capable of exhibiting catalytic activity include noble metals, e.g. gold, platinum, rhodium, palladium, ruthenium, rhenium, and silver; base metals such as copper, chromium, iron, cobalt, nickel, zinc, manganese, vanadium, titanium, scandium, and combinations of these. Solid state compounds suitable for use as catalytic species include, but are not limited to, oxides, nitrides and carbides, and one particular example of a class of solid state compounds useful as a catalytic species are the perovskite-type catalysts that comprise a metal oxide composition, such as those described by Golden, U.S. Pat. No. 5,939,354. Exemplary molecular catalytic species include at least metal Schiff base complexes, metal phosphine complexes and diazaphosphacycles. Non-limiting examples of enzymes useful as catalytic species include lipases, lactases, dehalogenases or combinations of these, with preferred enzymes being lipases, lactases or combinations thereof. Typically, metals are utilized as the catalytic species in catalysts contemplated for use in epoxidation processes, and silver in particular, is preferred.

The desired catalytic species, or precursor thereof, is provided in an impregnation solution, and the exposed carrier brought into contact with the same, before, during, after, or all of these, being exposed to the vacuum. Typically, the carriers will be impregnated one or more times with impregnation solutions, and desirably will be impregnated while still under vacuum. In some embodiments, the carriers are contacted with the impregnation solution at least twice, and in between, are removed from the vacuum to which the carriers were exposed. In any subsequent impregnations, the applied vacuum may be the same, or different, than that applied in the initial impregnation.

When the desired catalytic species comprises silver, the impregnations will desirably be sufficient to allow the silver to be provided on the carriers in an amount greater than 5 percent, greater than 10 percent, greater than 15 percent, greater than 20 percent, greater than 25 percent, preferably, greater than 27 percent, and more preferably, greater than 30 percent by weight, based on the weight of the catalyst. Although the amount of silver utilized is not particularly limited, the amount of silver provided in connection with the carriers may usually be less than 70 percent, and more preferably, less than 50 percent by weight, based on the weight of the catalysts.

Although silver particle size in the finished catalysts is important, the range is not narrow. A suitable silver particle size can be in the range of from 10 angstroms to 10,000 angstroms in diameter. A preferred silver particle size ranges from greater than 100 angstroms to less than 5,000 angstroms in diameter. It is desirable that the silver be relatively uniformly dispersed within, throughout, and/or on the carrier, and the same can be assisted by exposure of the carrier(s) to the vacuum as described.

Catalysts according to the present invention desirably comprise rhenium, and may, in certain embodiments, further include one or more additional promoters, such as, e.g., cesium. Rhenium promoted supported silver containing catalysts are known from U.S. Pat. No. 4,761,394 and U.S. Pat. No. 4,766,105. Broadly, the catalysts comprise silver, rhenium or compound thereof, and in some embodiments, a co-promoter such as a further metal or compound thereof and optionally an additional co-promoter such as one or more of molybdenum, tungsten, lithium, sulfur, manganese, rubidium, cesium, sodium, sulfur, phosphorus, boron, and compounds thereof, on the support material.

As is known to those skilled in the art, there are a variety of known promoters, or materials which, when present in combination with particular catalytic materials, e.g., silver, benefit one or more aspects of catalyst performance or otherwise act to promote the catalyst's ability to make a desired product, e.g., ethylene oxide or propylene oxide. More specifically, and while such promoters in themselves are generally not considered catalytic materials, they typically may contribute to one or more beneficial effects of the catalysts' performance, for example enhancing the rate, or amount, of production of the desired product, reducing the temperature required to achieve a suitable rate of reaction, reducing the rates or amounts of undesired reactions, etc. Furthermore, and as those of ordinary skill in the art are aware, a material which can act as a promoter of a desired reaction can be an inhibitor of another reaction. For purposes of the present invention, a promoter is a material which has an effect on the overall reaction that is favorable to the efficient production of the desired product, whether or not it may also inhibit any competing reactions that may simultaneously occur.

Known promoters for silver-based, epoxidation catalysts, in addition to rhenium, include, but are not limited to, molybdenum, tungsten, lithium, sodium, manganese, rubidium, and cesium. Rhenium, molybdenum or tungsten may suitably be provided as oxyanions, for example, as perrhenate, molybdate, or tungstate, in salt or acid form. Examples of promoters, their characteristics, and methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261.

Catalysts comprising silver as a catalytic species as well as at least rhenium as a promoter are expected to find particular benefit when the present methods are applied thereto. The rhenium component can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide may also be used. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

In some embodiments, catalysts comprising silver and rhenium, may additionally comprise a promoting amount of at least one further metal, a promoting amount of rhenium, and optionally a co-promoter. More specifically the further metal is selected from the group of Group IA metals, Group IIA metals, molybdenum, tungsten, chromium, titanium, hafnium, zirconium, vanadium, thallium, thorium, tantalum, niobium, gallium and germanium and mixtures thereof. Preferably the further metal is selected from the Group IA metals such as lithium, potassium, rubidium, sodium and cesium and/or from the Group IIA metals such as calcium and barium. More preferably, the further metal comprises lithium, sodium and/or cesium. Most preferably, is the further metal comprises cesium. Where possible, rhenium, the further metal or the co-promoter is provided as an oxyanion, in salt or acid form. Optional co-promoters include, but are not limited to, tungsten, manganese, molybdenum, chromium, sulfur, phosphorous, boron, and mixtures thereof.

The rhenium and any other desired promoters included in the catalyst are desirably provided in a promoting amount, and such amounts are readily determined by those of ordinary skill in the art. A "promoting amount" of a certain promoter refers to an amount of that promoter that works effectively to provide an improvement in one or more of the properties of a catalyst comprising the promoter relative to a catalyst not comprising said promoter. Examples of catalytic properties include, inter alia, operability (resistance to run-away), selectivity, activity, conversion, stability and yield. The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects. Generally speaking, promoting amounts of rhenium may be at least 1 ppmw, at least 5 ppmw, or between from 10 ppmw to 2000 ppmw, often between 20 ppmw and 1000 ppmw, calculated as the weight of rhenium based on the total weight of the catalyst.

Other promoters and/or co-promoters vary in concentration from 0.0005 to 1.0 wt. %, preferably from 0.005 to 0.5 wt. %. For some, e.g., cationic promoters, amounts between 10 ppm and 4000 ppm, preferably 15 ppm and 3000 ppm, and more preferably between 20 ppm and 2500 ppm by weight of cation calculated on the total support material are appropriate. Amounts between 50 ppm and 2000 ppm are frequently most preferable. If cesium is used in mixture with other cations, the ratio of cesium to any other cation(s), may vary from 0.0001:1 to 10,000:1, preferably from 0.001:1 to 1,000:1.

One particular example of an epoxidation of commercial importance is the epoxidation of alkylenes, or mixtures of alkylenes. Many references describe these reactions, representative examples of these being Liu et al., U.S. Pat. No. 6,511,938 and Bhasin, U.S. Pat. No. 5,057,481, as well as the Kirk-Othmer Encyclopedia of Chemical Technology, 4$^{th}$ Ed. (1994) Volume 9, pages 915-959.

The performance of catalysts in these reactions is typically evaluated on the basis of the catalysts' selectivity, activity, and stability during the epoxidation reactions. Stability typically refers to how the selectivity or activity of the process changes during the time that a particular batch of catalyst is being used, i.e., as more olefin oxide is produced. Catalysts of the present invention are expected to provide advantages in selectivity, activity and/or stability resulting from either the catalytic species loading that can be achieved. Advantage may also be seen in the lower production and/or equipment cost associated with the method (i.e., from requiring a lower level of vacuum than conventional methods).

Epoxidation reaction may take place in any suitable reactor, for example, fixed bed reactors, continuous stirred tank reactors (CSTR), and fluid bed reactors, a wide variety of which are well known to those skilled in the art and need not be described in detail herein. The desirability of recycling unreacted feed, employing a single-pass system, or using successive reactions to increase ethylene conversion by employing reactors in series arrangement can also be readily determined by those skilled in the art. The particular mode of operation selected is usually dictated by process economics. Conversion of olefin (alkylene), preferably ethylene, to olefin oxide, preferably ethylene oxide, can be carried out, for example, by continuously introducing a feed stream containing alkylene (e.g., ethylene) and oxygen or an oxygen-containing gas to a catalyst-containing reactor at a temperature of from 200° C. to 300° C., and a pressure which may vary between 5 atmospheres (506 kPa) and 30 atmospheres (3.0 MPa), depending upon the mass velocity and productivity desired. Residence times in large-scale reactors are generally on the order of from 0.1 seconds to 5 seconds. Oxygen may be supplied to the reaction in an oxygen-containing stream, such as, air or as commercial oxygen, or as oxygen-enriched air. The resulting alkylene oxide, preferably ethylene oxide, is separated and recovered from the reaction products using conventional methods.

Any alkylene can be utilized in the process, and examples of those that may desirably be epoxidized include, but are not limited to, 1,9-decadiene, 1,3-butadiene, 2-butene, isobutene, 1-butene, propylene, ethylene, or combinations of these. Preferably, the alkylene comprises ethylene.

Typically, epoxidation reactions may desirably be carried out in the gas phase, with a feed comprising the desired alkylene and oxygen being caused to come in contact with an epoxidation catalyst. Oftentimes, the catalyst is present as a solid material, and more particularly, may be present as a packed bed within the desired reactor. The quantity of catalyst used may be any suitable amount and will depend upon the application. In pilot plant reactors, the quantity of catalyst may be, e.g., less than 5 kg, while in commercial epoxidation plants, the quantity of catalyst used in the packed bed may be at least 10 kg, or at least 20 kg, or from $10^2$ to $10^2$ kg or from $10^3$ to $10^6$ kg.

Many epoxidation reactions are carried out as continuous processes, and the same is contemplated here. In such processes, the desired reactor may typically be equipped with heat exchange equipment to control the temperature of the process, within the reactor and/or the catalyst bed.

In one embodiment, the process for the oxidation of an alkylene comprises contacting a reaction mixture feed comprising an alkene, oxygen, and carbon dioxide, with a catalyst comprising a carrier and, deposited on the carrier either before, during, or after the carrier is exposed to the vacuum as described, silver, a rhenium promoter, a first co-promoter, and a second co-promoter; wherein the carbon dioxide is present in the reactor mixture in a quantity of at most 3 mole percent based on the total reaction mixture; the first co-promoter is selected from sulfur, phosphorus, boron, and mixtures thereof; and the second co-promoter is selected from tungsten, molybdenum, chromium, and mixtures thereof.

The alkylene oxide produced by the present epoxidation process may typically be processed to provide further downstream products, such as, for example, 1,2-diols, 1,2-diol ethers, 1,2-carbonates, and alkanolamines. Since the present invention provides an improved epoxidation method, it is contemplated that the improvements provided will carry forward to provide improvements to these downstream processes and/or products. Improved methods for the production of 1,2-diols, 1,2-diol ethers, 1,2-carbonates, and alkanolamines are thus also provided herein.

The conversion of alkylene oxides into 1,2-diols or 1,2-diol ethers may comprise, for example, reacting the desired alkylene oxide with water, suitably in the presence of an acidic or basic catalyst. For example, for preferential production of the 1,2-diol over the 1,2-diol ether, the alkylene oxide may be reacted with a tenfold molar excess of water, in a liquid phase reaction in the presence of an acid catalyst, e.g., 0.5-1.0 wt. % sulfuric acid, based on the total reaction mixture, at 50° C. to 70° C. at 1 bar absolute, or in a gas phase reaction, at 130° C. to 240° C. and from 20 bar to 40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternative 1,2-diol ethers may be prepared by converting the alkylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of alkylene oxides produced via the method of the present invention into alkanolamines may comprise, for example, reacting the alkylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897.

Some embodiments of the invention will now be described in detail in the following examples.

Example 1

Properties of the carriers used for the preparation of catalysts are given below.

| Carrier | Surface area ($m^2/g$) | Pore volume (cc/g) | Median pore diameter (μm) |
|---|---|---|---|
| A | 1.11 | 0.51 | 9.8 |
| B | 0.84 | 0.26 | 1.1 |

Figure 1B:
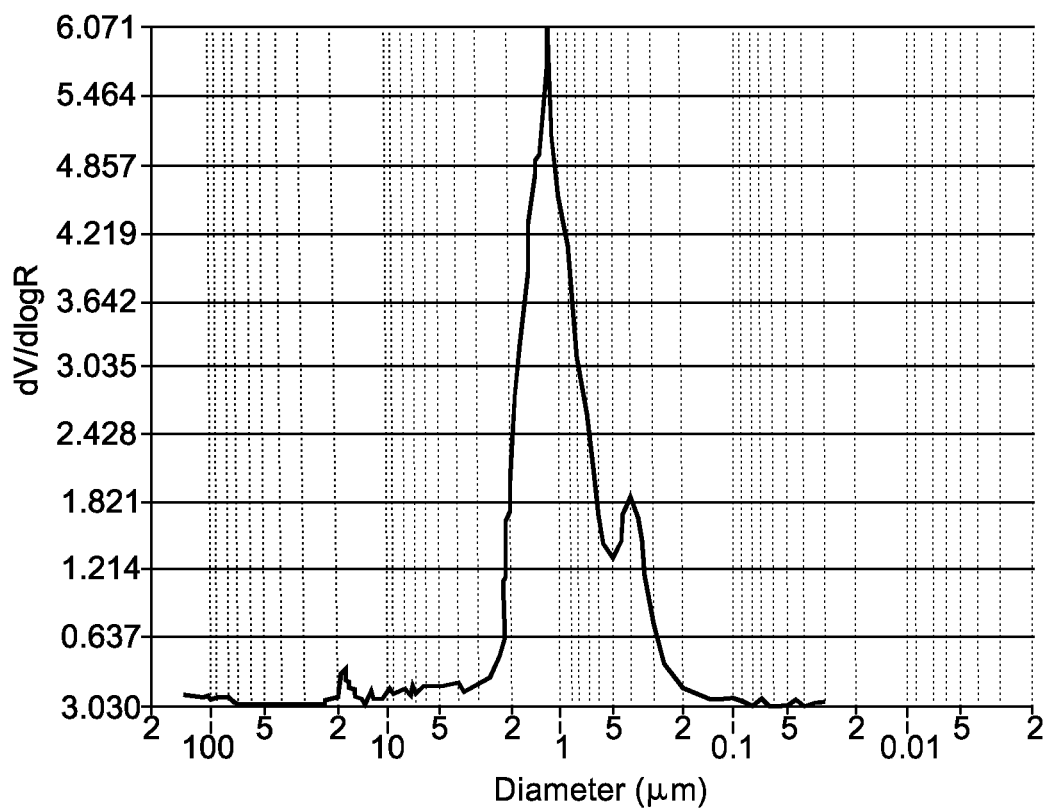
FIG. 1B is a graphical depiction of the pore size distribution of a carrier B to be subjected to a method according to one embodiment.
Figure 2A:
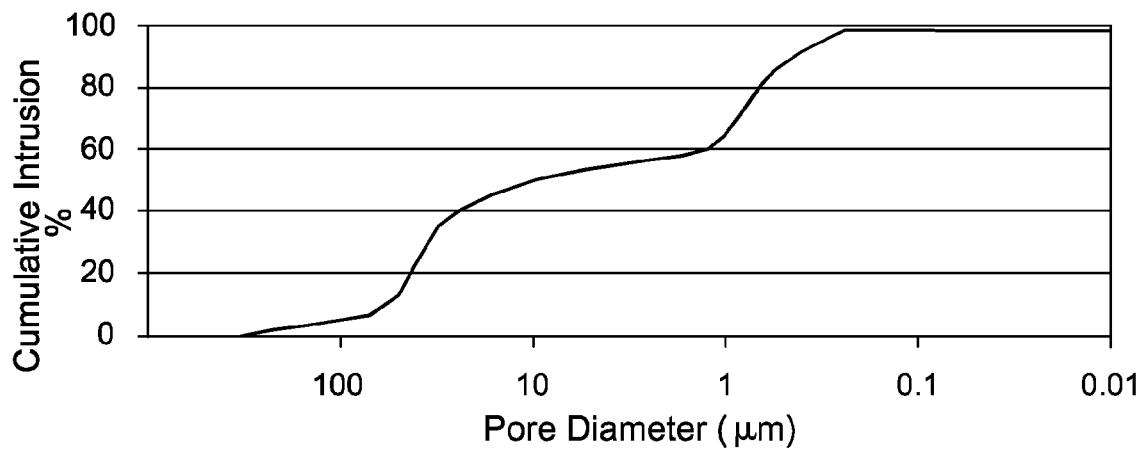
FIG. 2A is a graphical depiction of the cumulative intrusion during Hg porosimetry of a carrier A.
Figure 2B:
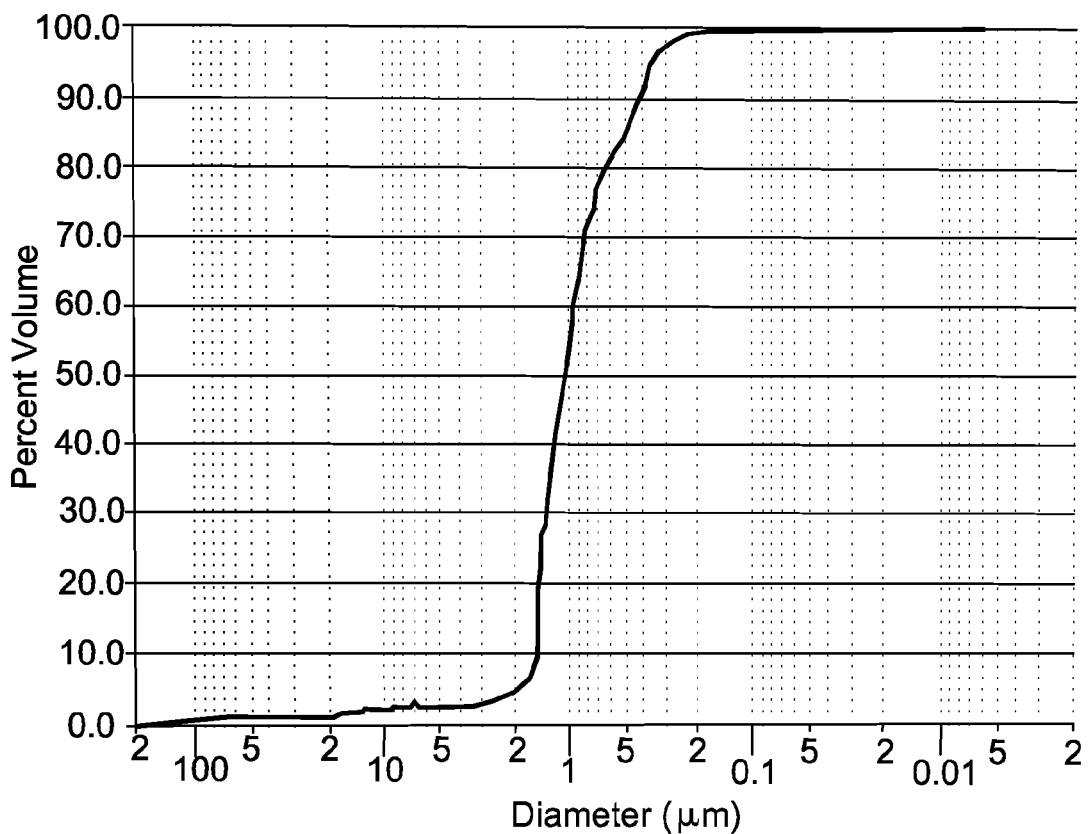
FIG. 2B is a graphical depiction of the cumulative intrusion during Hg porosimetry of a carrier B.

Carrier A is a conventional alpha-alumina support modified with 2 wt. % zircon and Carrier B is a commercially available conventional alpha-alumina support with product designation SA-5202. Both carriers are obtained from Saint-Gobain N or Pro (Stow, Ohio, USA). The pore size distributions measured as the differential intrusion curves obtained by mercury porosimetry are shown in FIGS. 1A and 1B for Carriers A and B, respectively, while their cumulative intrusion curves are shown in FIGS. 2A and 2B.

Preparation of Catalysts

The catalysts are prepared by vacuum impregnation of the above-identified carriers with silver-amine-oxalate solution prepared as described under "Catalyst Preparation" in US 2009/177000 A1 (26 wt. % Ag).

The carrier is placed in an appropriately sized glass cylindrical vessel which is equipped with suitable stopcocks for impregnating the carrier under vacuum. A suitable separatory funnel which is used for containing the impregnation solution is inserted through a rubber stopper into the top of the impregnation vessel. The impregnation vessel is connected to a mechanical vacuum pump and the pressure within the impregnation vessel is monitored using HIND HIVAC PIRANI GAUGE DHPG-222.

The impregnation vessel containing the carrier is evacuated to the desired vacuum level and held for 15 minutes, after which the impregnation solution is slowly added to the carrier by opening the stopcock between the separatory funnel and the impregnation vessel. After all the solution empties into the impregnation vessel (~15 seconds), the vessel is open to atmosphere and the mechanical vacuum pump is turned off. Following addition of the solution, the carrier remains immersed in the impregnation solution at ambient conditions for 15 minutes, and is thereafter drained of excess solution for 45 minutes.

The impregnated carrier is then dried as follows. The wet impregnated carrier pills are spread out in a monolayer on a stainless steel wire mesh tray (SS-316 with a 10.5 cm×8 cm square SS mesh with 1 mm apertures welded on the top) and introduced into a box furnace (Thermolyne—4800, ThermoFisher make, Barnstead, operating temperature range 100-1200° C.). Before introducing the impregnated carrier into the box furnace, the furnace is preheated to 100° C. The furnace is switched off prior to opening the door of the furnace to place the tray. A pair of tongs is used for transferring the tray into and out of furnace. The furnace is switched on and the impregnated carriers are dried for 30 minutes. The dried impregnated carriers are taken out from the box furnace and cooled in the open air.

The dried impregnated carriers are then roasted using a Hot Air Gun (Model number HL16105, Stetinel make with 1600 W output and power supply of 230-240V, 50 Hz.) as follows. An insulated divergent nozzle is made that can be fixed to the mouth of the hot air gun. The nozzle is 6 inches (15 cm) long and diameter at the top of the nozzle is 5.5 cm, which is approximately twice that of the hot air gun mouth. Temperature measurements at the top of the nozzle show that at setting 1, the measured temperature is 300±10° C., and with setting 2, it is 400±10° C. A mesh basket allows the impregnated carriers to be placed at exactly the same position at the top of the nozzle during roasting. After being roasted with setting 1 for 1.5 minutes and setting 2 for 2 minutes, the carriers are cooled in the open air to room temperature and weighed.

The carriers are then again impregnated with a silver-amine-oxalate solution. The impregnation, draining, drying and roasting steps for this second impregnation are carried out analogously to the first impregnation. The twice-impregnated carrier, that is now the finished catalyst, is again weighed. Based upon the weight gain of the carrier in the impregnation, the weight percent of silver is calculated.

Figure 3A:
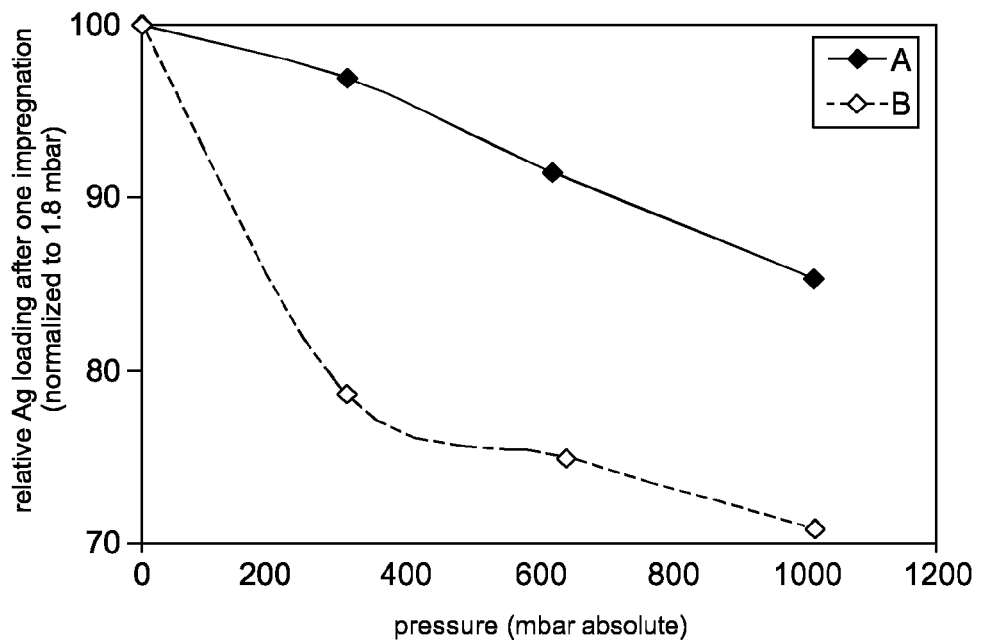
FIG. 3A is a graphical depiction of the relationship between minimum residual pressure (absolute) before Ag-solution impregnation and Ag loading on carriers A and B after a first impregnation with an Ag-solution.
Figure 3B:
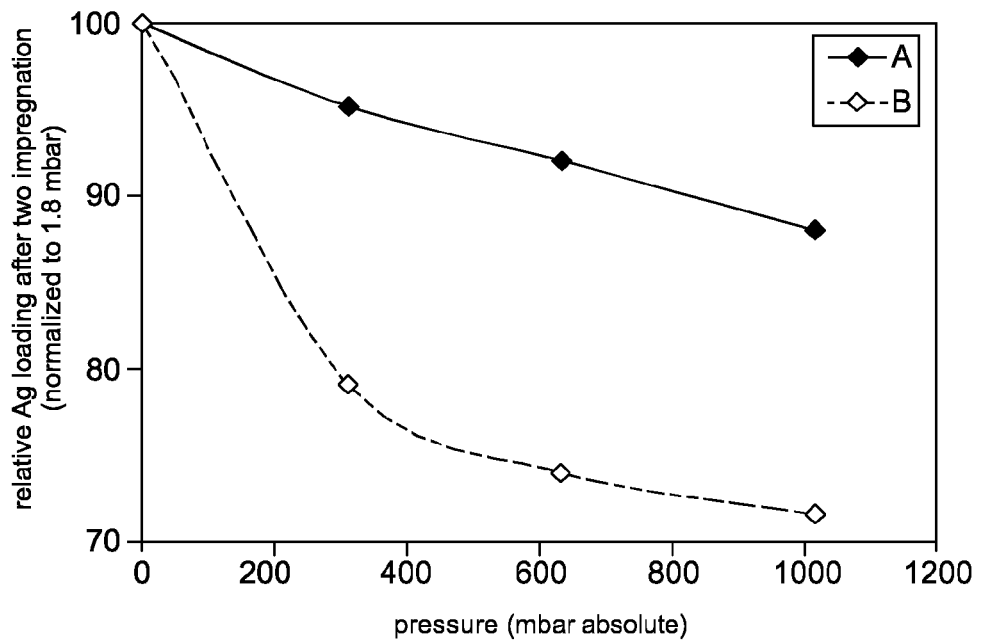
FIG. 3B is a graphical depiction of the relationship between minimum residual pressure (absolute) before Ag-solution impregnation and total Ag loading on carriers A and B after two impregnations with an Ag-solution.

Catalysts are prepared using both carrier A and carrier B at different vacuum levels according to the above protocol. For each experiment, the target vacuum level is achieved by evacuating the vessel containing the impregnated carrier from atmospheric pressure to the target vacuum level. The particular vacuum conditions employed and the silver loading achieved are shown in Tables 1 and 2, below, and FIG. 3A (silver loading after the first impregnation) and FIG. 3B (total silver loading after both impregnations). The pressures shown in FIGS. 3A and 3B are represented as the minimum residual pressures. Relative Ag loading of 100 percent is assumed at the lowest pressure level in Tables 1 and 2 in order to normalize the data with respect to total pore volume.

TABLE 1

Silver loading on carrier A at different vacuum levels

| Minimum residual pressure (mbar, absolute); 1st impregnation | 1st dip relative Ag loading (normalized to 1.8 mbar value) | Minimum residual pressure (mbar, absolute); 2nd impregnation | Total relative Ag loading (normalized to 1.8 mbar value) |
|---|---|---|---|
| 1.8 | 100 | 1.8 | 100 |
| 310 | 97 | 310 | 95 |
| 620 | 91 | 630 | 92 |
| 1013.25 | 85 | 1013.25 | 88 |

TABLE 2

Silver loading on carrier B at different vacuum levels

| Minimum residual pressure (mbar, absolute); 1st impregnation | 1st dip relative Ag loading (normalized to 1.8 mbar value) | Minimum residual pressure (mbar, absolute); 2nd impregnation | Total relative Ag loading (normalized to 1.8 mbar value) |
| --- | --- | --- | --- |
| 1.8 | 100 | 1.8 | 100 |
| 310 | 79 | 310 | 79 |
| 640 | 75 | 630 | 74 |
| 1013.25 | 71 | 1013.25 | 72 |

The results in FIGS. 3A and 3B and Tables 1 and 2 show that the silver loading on the carrier is dependent upon the level of minimum residual pressure inside the impregnation vessel containing the carriers before and as the carriers are contacted with silver impregnation solution. More specifically, the silver loading on the carriers decreases to varying extents with an increase in minimum residual pressure inside the impregnation vessel containing the support.

In particular, for support A (having a bimodal pore size distribution and a higher percentage of total pore volume in pores >3 μm), the first impregnation and total relative silver loading with respect to 1.8 mbar values decrease to 85% and 88%, respectively, as the minimum residual pressure inside the impregnation vessel containing the support increases over the range from 1.8 mbar, absolute, to 1013.25 mbar, absolute. Even more striking, for support B (having mono-modal pore size distribution and a lower percentage of total pore volume in pores >3 μm), the first impregnation and total relative silver loading with respect to 1.8 mbar values decrease to just 71% and 72%, respectively, as the minimum residual pressure inside the impregnation vessel containing the support increases over the range from 1.8 mbar, absolute, to 1013.25 mbar, absolute.

In summary, these results indicate that adequate, and even optimized, silver loading can be provided on carriers using a lower level of vacuum than previously thought possible, i.e., it is not necessary to evacuate to minimum residual pressures of 20 mmHg or less, in order to provide catalysts having a desired degree of silver loading. Since there is no need to expose carriers to a very high vacuum level (e.g., to minimum residual pressures of 20 mmHg, absolute, or less) to produce catalysts, energy, time and cost savings are provided.

We claim:

1. A method for providing an ethylene oxide epoxidation catalyst comprising exposing a carrier to a vacuum having a minimum residual pressure of greater than 200 mbar, absolute, and thereafter contacting the carrier with an impregnation solution comprising a catalytic species or precursor thereof comprising silver, wherein the carrier has i) a surface area of at least 1.1 $m^2/g$ and ii) at least two pore size distribution peaks in the pore diameter range of from 0.01 microns to 100 microns and a median pore diameter greater than 1.1 micron.

2. The method of claim 1, wherein a catalytic species loading of at least 10 wt. % is provided on the carrier, based on the total weight of the epoxidation catalyst.

3. The method of claim 1, wherein the impregnation solution further comprises one or more promoters.

4. The method of claim 3, wherein the one or more promoters comprise rhenium and cesium.

5. An epoxidation catalyst prepared according to the method of claim 1.

6. A method for the epoxidation of one or more alkylenes comprising contacting an oxygen source and an alkylene in the presence of an epoxidation catalyst prepared according to the method of claim 1.

7. The method of claim 6, wherein the alkylene comprises ethylene.

8. A method for making a 1,2-diol, a 1,2-diol ether, a 1,2-carbonate, or an alkanolamine comprising converting an alkylene oxide prepared according to the method of claim 6 into the 1,2-diol, a 1,2-diol ether, a 1,2-carbonate, or alkanolamine.

9. The method of claim 1, wherein the carrier has at least 5% of its total pore volume being present in pores having a pore diameter of greater than 3 microns.

\* \* \* \* \*